United States Patent [19]

Olson

[11] 4,012,290
[45] Mar. 15, 1977

[54] ELECTROCHEMICAL DETECTION FOR LEAD ALKYLS

[75] Inventor: Donald C. Olson, Florissant, Mo.

[73] Assignee: Shell Oil Company, Houston, Tex.

[22] Filed: Jan. 23, 1976

[21] Appl. No.: 651,679

Related U.S. Application Data

[62] Division of Ser. No. 501,513, Aug. 29, 1974, Pat. No. 3,960,690.

[52] U.S. Cl. .................................................. 204/1 T
[51] Int. Cl.² ........................................ G01N 27/46
[58] Field of Search ................ 204/1 T, 1 K, 195 R

[56] References Cited

UNITED STATES PATENTS

| | | | |
|---|---|---|---|
| 3,305,457 | 2/1967 | Hyman | 204/1 K |
| 3,355,367 | 11/1967 | Marsh | 204/195 W |
| 3,519,547 | 7/1970 | Paulik et al. | 204/195 R |
| 3,586,608 | 6/1971 | Juda et al. | 204/1 K |
| 3,926,558 | 12/1975 | Davis | 204/1 T |

*Primary Examiner*—T. Tung

[57] ABSTRACT

A method and apparatus for measuring trace amounts of lead alkyls in gasoline wherein a small sample of the gasline is injected into a vaporizer, with a carrier gas transporting the sample through the vaporizer to a filter that separates the interfering olefins and aromatic components from the lead alkyls in the sample. The discharge from the filter is supplied to an electrochemical cell of a type known as a galvanic sensor whose output signal is integrated or otherwise utilized to obtain a measurement of the quantity of lead alkyls in the sample.

4 Claims, 3 Drawing Figures

ELECTROCHEMICAL DETECTION FOR LEAD ALKYLS

This is a division of application Ser. No. 501,513, filed Aug. 29, 1974, now U.S. Pat. No. 3,960,690.

BACKGROUND OF THE INVENTION

The present invention relates to a method and apparatus for measuring trace amounts of lead alkyls in hydrocarbons particularly gasoline. Where government regulations require that major distributors of gasoline market at least one unleaded grade of gasoline, this is allowed to contain no more than 0.05 grams of lead per gallon. This quantity of lead is equal to approximately 17 parts per million (ppm) by weight. With these regulations in effect, there is a need for a simple, rapid, inexpensive and reliable method for determining the quantity of lead in gasoline. Preferably, the method used should be relatively simple so that it may be used by people who are not skilled in chemistry or other technical arts. In addition, since many tests must be conducted, the equipment and the cost of conducting the tests must be relatively low. Further, the test must be accurate and not require additional laboratory analysis and must be repeatable so that uniform results may be obtained on all samples.

At present, the only methods available for determining trace amounts of lead in gasoline are variations of the same method which involve the chemical oxidation of the lead followed by a colorimetric determination of the oxidation products. These methods being basically chemical methods require the availability of several reagents that results in a complicated method. All of these problems lead to considerable question of whether the results obtained by any one operator are comparable to those obtained by a different operator operating on a different sample with different reagents.

BRIEF SUMMARY OF THE INVENTION

The present invention solves the above problems by providing a completely automatic apparatus for measuring trace lead content of hydrocarbon material particularly gasoline. The method used involves the steps of vaporizing a small sample of the gasoline containing the trace amounts of lead, separating the interfering aromatics and olefin components from the lead alkyls in the vaporized sample and passing the sample to an electrochemical cell. The electrochemical cell comprises two platinum electrodes, and an electrolyte, for example, the silver nitrate in butanol-water solution. other appropriate electrolytes (for example, silver nitrate in isopropanol, acetonitrile, or diglyme) may also be used. The current produced by the electrochemical cell is integrated, with the sum of the integration being displayed on a meter which may be calibrated directly in ppm of lead.

The apparatus utilizes a vaporizing furnace which preferably has a large heat sink so that temperature variations when a cold sample is injected are very small. The sample may be injected into the furnace using a conventional hypodermic needle and a septum as used in chromatograph equipment. A carrier gas is used to transport the sample through the furnace and the remainder of the apparatus. While various types of carrier gas may be used, it is found that conventional Freon is a satisfactory carrier gas and readily available. Preferably the carrier gas is saturated with water before it is introduced into the furnace. The gas exits from the furnace and is passed through a filter for separating the aromatic and olefinic components from the lead alkyls in the vaporized sample. The filter may comprise a short section of a conventional chromatograph column which is filled with material which will absorb or retard both the olefinic and aromatic components. The sample is discharged from the filter into the electrochemical cell whose output is directly related to the lead alkyl content of the gasoline. The use of an electrochemical cell having platinum electrodes and silver nitrate in butanol-water as an electrolyte produces a cell that is relatively insensitive to the conventional additives used in gasoline and responds almost exclusively to the lead alkyls. The signal from the cell is preferably integrated so that the total quantity of lead in the sample is actually measured. The integration may be accomplished with an electronic integrator whose output is displayed on a meter or by manual integration of the signal recorded with a chart recorder. The preferred method is to utilize the integrated result. However, peak height of the signal can also be used as a simpler method to measure Pb content of the sample if the peak width does not change with sample composition.

BRIEF DESCRIPTION OF THE DRAWINGS

The present invention will be more easily understood from the following detailed description of a preferred embodiment when taken in conjunction with the attached drawings in which.

PREFERRED EMBODIMENT

Figure 1:
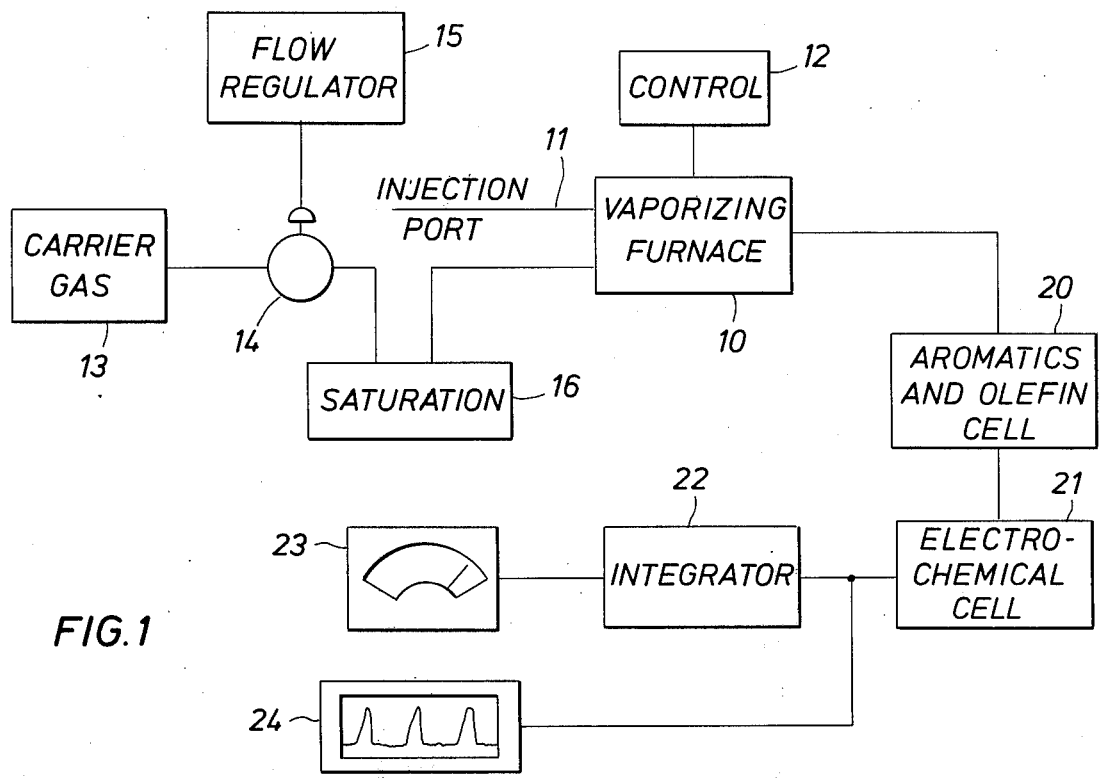
FIG. 1 is a block diagram of an apparatus for performing the method of the present invention.

Referring now to FIG. 1, there is shown a vaporizing furnace 10 having an injection port 11 for injecting a sample into the furnace. As explained above, the injection port may comprise a conventional rubber septum as used in chromatographic units for injecting samples into chromatographic columns. In the manner, very accurate samples may be measured by the use of a hypodermic needle and injected into the furnace. It has been found that samples in the range of 5 to 10 microliters provide satisfactory results although of course, larger or smaller samples could be used. The use of larger samples, of course, would decreased the useful lifetime of the aromatics-and-olefin filter described below. The vaporizing furnace is preferably electrically heated with its temperature being controlled by temperature control 12. The temperature control need not be unduly complicated and may comprise a conventional thermostat, for example, a thermostat Model ANS 221,23 manufactured by the Fenwal Company of Ashland, Massachusetts. Further, the furnace may be a relatively simple design, for example, a large block of aluminum which will act as a heat sink and having suitable passageways for injecting the sample and heating the sample.

The sample is carried through the furnace to the remainder of the equipment by carrier gas supplied from a source 13 through a flow regulator 14. The flow regulating valve 14 is positioned by a regulator 15 and both units may comprise a simple mechanical flow regulator. After passing through the flow regulating valve, the carrier gas passes through a saturator 16 where it is saturated with water and is then introduced into the vaporizing furnace. As explained above the carrier gas may comprise any inert gas such as nitrogen or the like although excellent results have been obtained using commercial Freon that is supplied in small pressurized containers. This is particularly desirable since the containers are widely available in the commercial market, and no special equipment is necessary to obtain a carrier gas supply.

After the sample is vaporized, it exits from the furnace 10 and enters the aromatics/olefin filter 20. This filter is designed to separate both the interfering aromatics and the olefinic components from the lead alkyls in the gasoline since the electrochemical cell used for detecting the trace amounts of lead in the gasoline responds somewhat to aromatics and olefins. The filter may be a relatively simple design, for example, a short length of glass tubing may be filled with conventional chromatographic partitioning materials. In particular, the glass tubing may be closed at one end with a pyrex glass wool plug and then a short section, for example, 2 inches, filled with a 20% Carbowax 600 saturated with silver nitrate disposed on a 30/60 Chromosorb W support. The Chromosorb W should previously have been coated with an 8% solution of potassium hydroxide. All of these materials are available from Applied Science Laboratories, Inc. of State College, Pennsylvania. Next, a short pyrex glass wool plug is placed in the tube, and another partitioning material of two inches disposed in the tube with the second material comprising a CYCLO-N on Chromosorb W, also available from Applied Science Laboratories. In using this type of filter, the flow of the vaporized sample and carrier gas should be in the direction of first through the $AgNO_3$ in Carbowax and then through the CYCLO-N material. In addition, the filter should be heated so that the vaporized material does not condense in the filter. This may be readily accomplished by surrounding the short glass tube with a resistance heater and utilizing a temperature control to control the power to the heater. For example, a 25-watt heater may be placed around the filter and its power controlled by the temperature controller known as an RCA (Radio Corporation of America) Model CA3059 control.

After the olefins and the aromatics have been separated, the sample is passed to the electrochemical cell 21. As explained above, the cell comprises a platinum counter electrode and an indicator electrode separated by a suitable electrolyte. Satisfactory results have been obtained by using a silver nitrate solution in isopropyl alcohol-water. Also, a 10% solution of silver nitrate in butanol containing 10% water has been used. The lead alkyls reduce the silver ions from the silver nitrate to metallic silver (or an unstable silver alkyl intermediate) which is deposited on the indicator electrode followed by the production of electrical current between the electrodes as the silver (or silver alkyl) is oxidized. Other materials which undergo similar redox reactions with lead alkyls might also be suitable electrolytes for the cell; for example, mercuric ion or cupric ion, both of which are reduced by lead alkyls. Various solvents capable of dissolving both the metallic salt and the lead alkyl may be used, for example, cetonitrile or diglyme.

The current from the electrochemical cell is integrated by a circuit 22 so that the total current produced is measured which is directly related to the amount of lead alkyls in the gasoline sample can be determined. The product of the integration may be displayed on a meter movement 23 whose scale can be calibrated in parts per million (ppm) of lead and/or recorded on a chart recorder 24. Of course, if the signal is recorded on a chart recorder, it will be necessary to integrate the area under the peak to obtain the total quantity of lead in the gasoline. When the term "lead alkyl" is used above, it refers to either tetraethyl lead or tetramethyllead or to chemically equilabrated mixture thereof or to physical mixtures thereof. Of course before the unit can be used to test unknown samples its response must be calibrated. This is a relatively simple procedure since a sample of standard solution can be injected into the apparatus and the range of the meter movement adjusted to correlate with the known ppm of lead in the standard sample. The same procedure can be used to check the performance of the apparatus.

Figure 2:
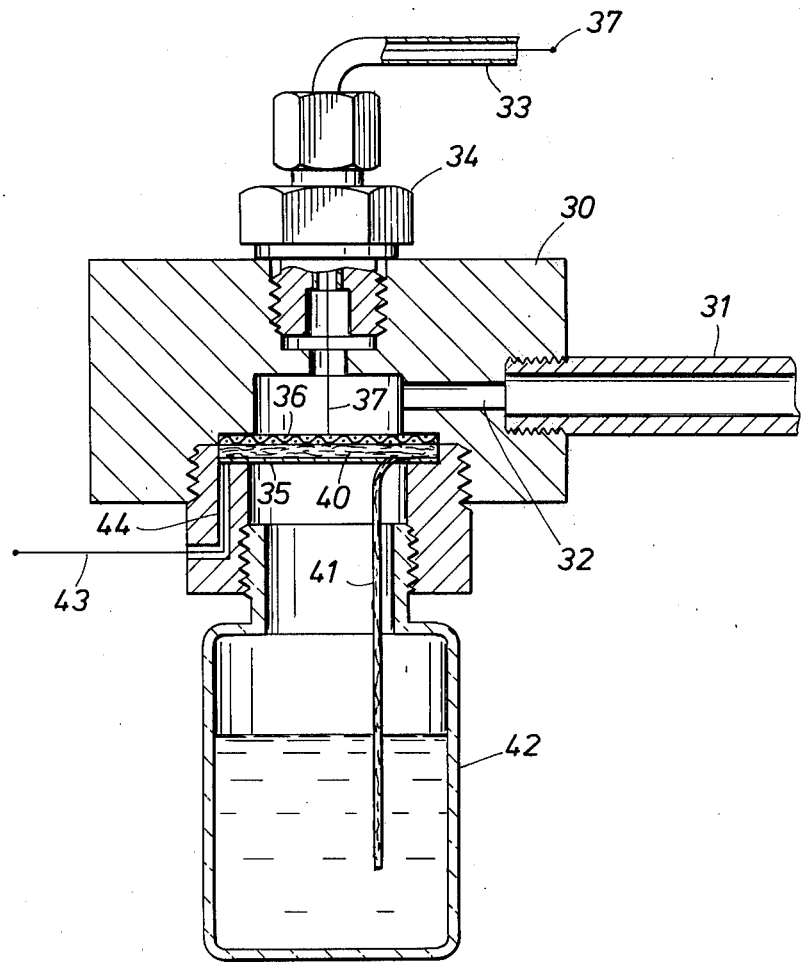
FIG. 2 is a vertical section of the electrochemical cell used in the apparatus of FIG. 1.

Referring to FIG. 2, there is shown on design of an electrochemical cell that can be used in the apparatus. This cell can be made relatively small since the amount of electrolyte required can be in the range of 1 to 2 cubic centimeters (in the reservoir). The cell has a main body 30 and threaded insert 45 having an inlet port 32. A short threaded tubular member 31 being secured in the end of the inlet port 32 to permit attachment of the electrochemical cell directly to the outlet of the filter by means of a tubing connector. The outlet of the cell is formed by means of a tube 33 disposed in a top cap 34 that threads into a central opening in the main body. The indicator electrode 36 is disposed in the top of the cell and may consist of a disc of approximately ½ inch in diameter formed from platinum screen wire having a 52 mesh of 38 gauge wire. Positioned below the indicate electrode is a second platinum electrode 35 that acts as the counter electrode. This electrode can also comprise ½ inch disc of platinum screen of the same type used for the electrode 36 or it may be of platinum foil. Positioned between the two electrodes is a disc of immobilized electrolyte 40 which may be formed from paper-type material, for example, filter paper or blotter paper which is impregnated with electrolyte. The immobilized electrolyte disc 40 is coupled to a wick 41 which extends into the reservoir of electrolyte solution contained in the small bottle 42. The small bottle 42 is threaded into a threaded bottom insert 45 in the bottom of the main body 30. The bottom closure also holds the combination of the immobilized electrolyte disc and counter electrode in their proper positions. The counter electrode is connected to a lead 43 that passes through an opening 44 formed in the insert 45 while the indicator electrode is connected to a lead 37 that passes out the outlet tube 33.

The above described electrochemical cell has the advantage of being small and easily transported. This also permits the cell to be mounted in the instrument by merely coupling the cell to the exit tubing of the aromatic-and-olefin filter 20. The use of the simple bottle 42 for containing a reservoir of electrolyte permits the cell to be transported in a dry condition with the only electrolyte being that immobilized in the electrolyte matrix and wick. Thus, when it is desired to use the apparatus, one only needs to place an electrolyte solution in the cell and the retained electrolyte in the wick and its extension will immediately supply sufficient electrolyte between the two electrodes of the cell. This is a distinct advantage on equipment which must be transported from location to location to make an analysis of lead in gasoline samples and operated by relatively unskilled personnel.

Figure 3:
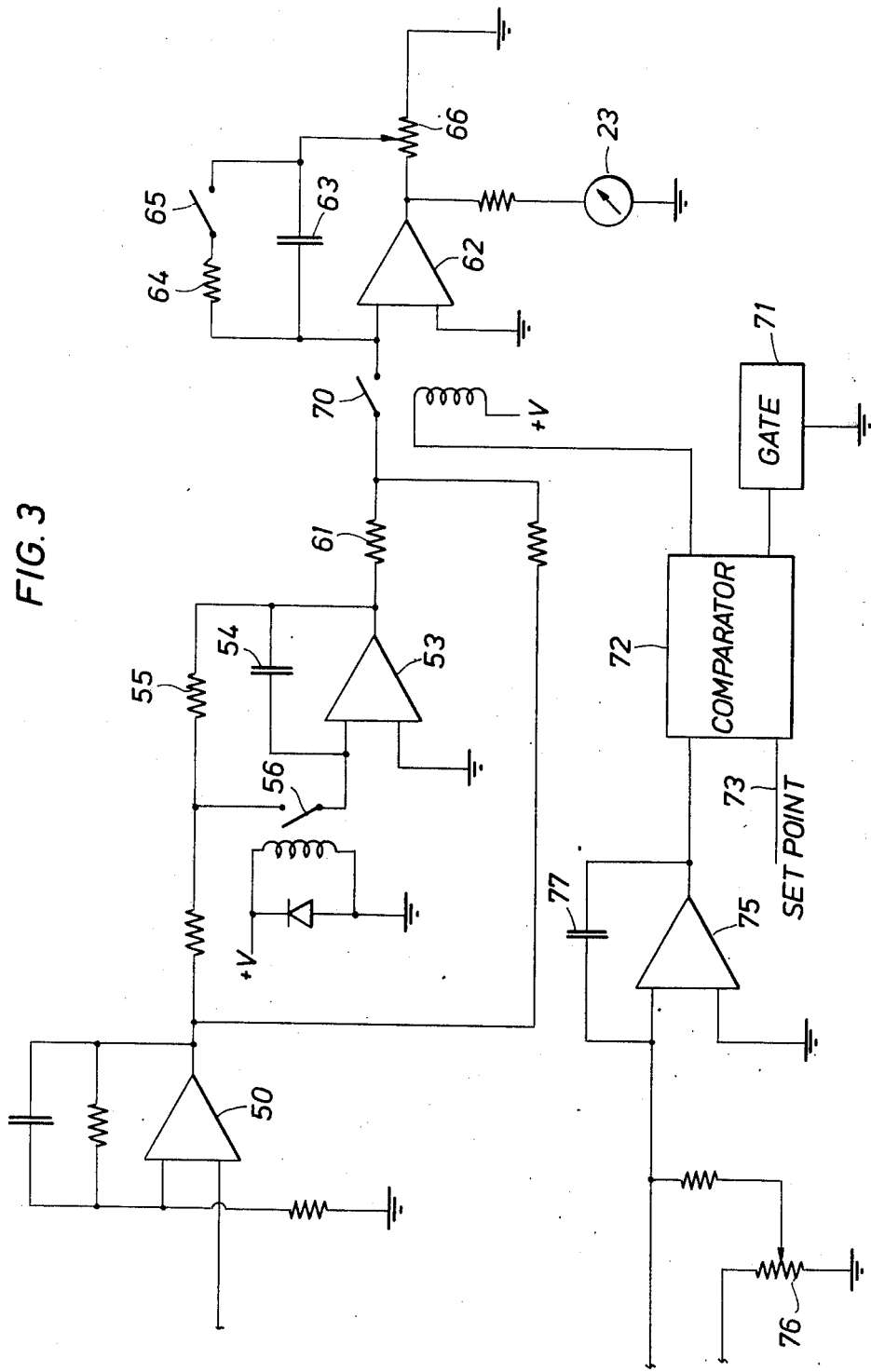
FIG. 3 is a schematic drawing of an integration circuit suitable for use with the apparatus of FIG. 1.

The integrating circuit is shown in FIG. 3 and comprises an input amplifier 50 which receives the signal over the lead 37 from the electrochemical cell. The amplifier 50 operates as an impedance matching device to match the impedance of the electrochemical cell to the integrating circuit. The integrating circuit comprises an amplifier 62 having a capacitor 63 disposed in its feedback circuit. The amplifier 62 is coupled through a resistor 60 and a lead 52 to the output of the amplifier 50. Also included in the circuit is an automatic zeroing circuit that is used to zero the instrument after the electrochemical cell has been installed and a flow of carrier gas initiated. This zero is necessary to eliminate noise and other extraneous signals caused by the carrier gas and the electrochemical cell. The zeroing circuit comprises an amplifier 53 having a capacitor 54 and a resistance 55 disposed in its feedback circuit. The feedback circuit of the amplifier is coupled by means of a solenoid operated switch 56 which is closed when it is desired to zero the instrument. Closure of the solenoid switch 56 also closes the switch 65 to place a corresponding resistance 64 in the feedback circuit of the amplifier 62. This will supply a voltage to the resistance 61 which is equal and opposite to the voltage supplied by the resistance 60 which will then permit the amplifier 62 to adjust the charge on the capacitor 63 to give a zero output. The output signal from the integrating circuit is supplied through an adjustable resistor 66 to the meter means 23. The resistor 66 provides a means for adjusting the span of the instrument so that its reading will equal the known lead content of a calibrating sample.

Under some conditions the gasoline does not return to zero after a peak but tails off. This occurs for example where olefins or aromatics in the sample pass through the filter 20. To eliminate the error a switch circuit is incorporated in the integrating circuit to terminate the integration a preset time after the sample is injected. The circuit utilizes a relay 70 to remove the signal from the integrating circuit. The relay is operated by a comparing circuit 72 and gate 71. The comparing circuit compares a preset voltage 73 with the amplitude of a ramp voltage 74. Thus by varying the preset voltage 73 the integration time can be varied.

The ramp voltage is produced by the amplifier 75, variable resistance 76 and capacitor 77 combination. The variable resistance provides additional means for varying the integration time period. The switch circuit is reset to zero by short circuiting the ramp voltage generator.

OPERATION

The above described instrument is operated by first filling the electrolyte container 42 of the electrochemical cell with a previously prepared electrolyte. The cell is then mounted in the instrument, the power turned on to various electronic circuits, and the flow of carrier gas is initiated. After the operation is stabilized, for example, two to three minutes of flow of carrier gas, a sample may be injected through the injection port of a vaporizing furnace. The remainder of the operation will be automatic and the quantity of lead in the sample can be read on the meter means 23 or recorded on the chart recorder 24. If it is desired to calibrate the instrument at the same time, a second sample having a known lead concentration can be injected and a correlating reading taken. From the two readings, it will be easy to determine the exact lead content of the unknown sample.

We claim as our invention:
1. A method for measuring trace amounts of lead alkyls in gasolines comprising:
    vaporizing a sample of the gasoline containing the trace amounts of lead alkyls;
    passing the vaporized sample through a filter to separate the interfering aromatic and olefin components from the lead alkyls in the sample;
    injecting the filtered sample into an electrochemical cell having an electrolyte; and
    measuring the current produced by the electrochemical cell.
2. The method of claim 1 wherein the net current signal produced by the electrochemical cell is integrated.
3. The method of claim 1 wherein the electrolyte in the cell comprises a metal salt and a solvent.
4. The method of claim 3 wherein the electrolyte in the cell is a solution of silver nitrate and aqueous butanol.

* * * * *